(12) United States Patent
Dugan et al.

(10) Patent No.: US 10,807,005 B2
(45) Date of Patent: *Oct. 20, 2020

(54) SYSTEMS AND METHODS FOR PROVIDING BIOFEEDBACK INFORMATION TO A CELLULAR TELEPHONE AND FOR USING SUCH INFORMATION

(71) Applicant: PEXS LLC, Hawthorne, NY (US)

(72) Inventors: Brian M. Dugan, Sleepy Hollow, NY (US); Steven M. Santisi, Ridgefield, CT (US); Jean Pierre Latrille, Sleepy Hollow, NY (US)

(73) Assignee: PEXS LLC, Hawthorne, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/141,967

(22) Filed: Sep. 25, 2018

(65) Prior Publication Data

US 2019/0022532 A1 Jan. 24, 2019

Related U.S. Application Data

(63) Continuation of application No. 15/591,084, filed on May 9, 2017, now Pat. No. 10,105,604, which is a
(Continued)

(51) Int. Cl.
*A63F 13/31* (2014.01)
*A63F 13/73* (2014.01)
(Continued)

(52) U.S. Cl.
CPC ............ *A63F 13/73* (2014.09); *A61B 5/0002* (2013.01); *A61B 5/681* (2013.01); *A63F 13/211* (2014.09);
(Continued)

(58) Field of Classification Search
CPC ..................................................... A63F 13/212
See application file for complete search history.

(56) References Cited

U.S. PATENT DOCUMENTS

| 3,834,702 A | 9/1974 | Bliss |
| 4,484,743 A | 11/1984 | Williams |

(Continued)

FOREIGN PATENT DOCUMENTS

| EP | 1 292 217 B1 | 11/2005 |
| EP | 1 639 939 A1 | 3/2006 |

(Continued)

OTHER PUBLICATIONS

Busch, Fritz "Diabetes Institute Brings Dakota, New Ulm Together" Jun. 10, 2001. Ogden Newspapers, Inc.
(Continued)

*Primary Examiner* — David L Lewis
*Assistant Examiner* — Shauna-Kay Hall
(74) *Attorney, Agent, or Firm* — Dugan & Dugan, PC

(57) ABSTRACT

The present invention provides systems, methods and apparatus for a wearable band adapted to be worn by a user. The wearable band may include one or more biometric sensors such as a pulse monitor adapted to monitor a pulse of the user, and a transmitter adapted to wirelessly transmit pulse information from the pulse monitor to a mobile device such as a cellular telephone or PDA. The wearable band does not include a display for the biometric information. Numerous additional embodiments are disclosed.

18 Claims, 4 Drawing Sheets

Related U.S. Application Data continuation of application No. 14/619,061, filed on Feb. 10, 2015, now Pat. No. 9,675,875, which is a continuation of application No. 12/538,862, filed on Aug. 10, 2009, now Pat. No. 8,976,007, which is a continuation-in-part of application No. 12/426,193, filed on Apr. 17, 2009, now abandoned.

(60) Provisional application No. 61/087,698, filed on Aug. 9, 2008, provisional application No. 61/045,955, filed on Apr. 17, 2008.

(51) Int. Cl.

| | | |
|---|---|---|
| *A61B 5/00* | (2006.01) | |
| *A63F 13/212* | (2014.01) | |
| *A63F 13/71* | (2014.01) | |
| *G01P 15/02* | (2013.01) | |
| *A63F 13/211* | (2014.01) | |
| *A63F 13/92* | (2014.01) | |
| *A61B 5/024* | (2006.01) | |

(52) U.S. Cl.
CPC ............ *A63F 13/212* (2014.09); *A63F 13/31* (2014.09); *A63F 13/71* (2014.09); *A63F 13/92* (2014.09); *G01P 15/02* (2013.01); *A61B 5/024* (2013.01); *A61B 2562/0219* (2013.01)

(56) References Cited

U.S. PATENT DOCUMENTS

| | | |
|---|---|---|
| 4,542,897 A | 9/1985 | Melton et al. |
| 4,735,410 A | 4/1988 | Nobuta |
| 4,817,938 A | 4/1989 | Nakao et al. |
| 4,858,930 A | 8/1989 | Sato |
| 4,976,435 A | 12/1990 | Shatford et al. |
| 5,001,632 A | 3/1991 | Hall-Tipping |
| 5,142,358 A | 8/1992 | Jason |
| RE34,728 E | 9/1994 | Hall-Tipping |
| 5,362,069 A | 11/1994 | Hall-Tipping |
| 5,377,100 A | 12/1994 | Pope et al. |
| 5,462,504 A | 10/1995 | Trulaske et al. |
| 5,515,865 A | 5/1996 | Scanlon |
| 5,527,239 A | 6/1996 | Abbondanza |
| 5,591,104 A | 1/1997 | Andrus et al. |
| 5,592,401 A | 1/1997 | Kramer |
| 5,624,316 A | 4/1997 | Roskowski et al. |
| 5,645,513 A | 7/1997 | Haydocy et al. |
| 5,667,459 A | 9/1997 | Su |
| 5,672,107 A | 9/1997 | Clayman |
| 5,702,323 A | 12/1997 | Poulton |
| 5,781,698 A | 7/1998 | Teller et al. |
| 5,885,156 A | 3/1999 | Toyohara et al. |
| 5,902,250 A | 5/1999 | Verrier et al. |
| 5,918,603 A | 7/1999 | Brown |
| 5,928,133 A | 7/1999 | Halyak |
| 5,947,868 A | 9/1999 | Dugan |
| 5,989,157 A * | 11/1999 | Walton .................. A63B 24/00 482/1 |
| 6,024,675 A | 2/2000 | Kashiwaguchi |
| 6,062,216 A | 5/2000 | Corn |
| 6,066,075 A | 5/2000 | Poulton |
| 6,152,856 A | 11/2000 | Studor et al. |
| 6,179,713 B1 | 1/2001 | James et al. |
| D439,981 S | 4/2001 | Kasabach et al. |
| 6,213,872 B1 | 4/2001 | Harada et al. |
| 6,244,988 B1 | 6/2001 | Delman |
| 6,251,010 B1 | 6/2001 | Tajiri et al. |
| 6,267,677 B1 | 7/2001 | Tajiri et al. |
| 6,302,789 B2 | 10/2001 | Harada et al. |
| D451,604 S | 12/2001 | Kasabach et al. |
| 6,347,993 B1 | 2/2002 | Kondo et al. |
| 6,354,940 B1 | 3/2002 | Itou et al. |
| 6,375,572 B1 | 4/2002 | Masuyama et al. |
| D460,971 S | 7/2002 | Sica et al. |
| 6,456,749 B1 | 9/2002 | Kasabach et al. |
| 6,482,092 B1 | 11/2002 | Tajiri et al. |
| 6,494,830 B1 | 12/2002 | Wessel |
| 6,513,160 B2 | 1/2003 | Dureau |
| 6,514,199 B1 | 2/2003 | Alessandri |
| 6,527,711 B1 | 3/2003 | Stivoric et al. |
| 6,579,231 B1 | 6/2003 | Phipps |
| 6,585,622 B1 | 7/2003 | Shum et al. |
| 6,595,858 B1 | 7/2003 | Tajiri et al. |
| 6,595,929 B2 | 7/2003 | Stivoric et al. |
| 6,605,038 B1 | 8/2003 | Teller et al. |
| 6,628,847 B1 | 9/2003 | Kasabach et al. |
| 6,641,482 B2 | 11/2003 | Masuyama et al. |
| 6,652,383 B1 | 11/2003 | Sonoda et al. |
| 6,705,972 B1 | 3/2004 | Takano et al. |
| 6,720,983 B1 | 4/2004 | Massaro et al. |
| 6,746,371 B1 | 6/2004 | Brown et al. |
| 6,758,746 B1 | 7/2004 | Hunter et al. |
| 6,786,825 B2 | 9/2004 | Kawazu |
| 6,796,927 B2 | 9/2004 | Toyama |
| 6,881,176 B2 | 4/2005 | Oishi et al. |
| 6,888,779 B2 | 5/2005 | Mollicone et al. |
| 6,902,513 B1 | 6/2005 | McClure |
| 6,966,837 B1 | 11/2005 | Best |
| 7,020,508 B2 | 3/2006 | Stivoric et al. |
| 7,041,049 B1 | 5/2006 | Raniere |
| 7,057,551 B1 | 6/2006 | Vogt |
| 7,068,860 B2 | 6/2006 | Kasabach et al. |
| 7,153,262 B2 | 12/2006 | Stivoric et al. |
| 7,261,690 B2 | 8/2007 | Teller et al. |
| 7,285,090 B2 | 10/2007 | Stivoric et al. |
| 7,628,730 B1 | 12/2009 | Watterson et al. |
| 7,749,056 B2 | 7/2010 | Ando et al. |
| 7,802,724 B1 * | 9/2010 | Nohr .................. G07C 9/00111 235/384 |
| 7,931,563 B2 | 4/2011 | Shaw et al. |
| 7,934,983 B1 | 5/2011 | Eisner |
| 7,946,959 B2 | 5/2011 | Shum et al. |
| 8,188,868 B2 | 5/2012 | Case, Jr. |
| 8,287,383 B1 | 10/2012 | Etter et al. |
| 8,287,436 B2 | 10/2012 | Shum et al. |
| 8,292,743 B1 | 10/2012 | Etter et al. |
| 8,313,416 B2 | 11/2012 | Ellis et al. |
| 8,444,491 B2 | 5/2013 | Bethke et al. |
| 8,491,395 B2 | 7/2013 | Auterio et al. |
| 8,496,532 B1 | 7/2013 | Bethke et al. |
| 8,506,409 B2 | 8/2013 | Bethke et al. |
| 8,556,778 B1 | 10/2013 | Dugan |
| 8,608,570 B1 | 12/2013 | Mahajan et al. |
| 8,784,273 B2 | 7/2014 | Dugan |
| 8,949,070 B1 * | 2/2015 | Kahn .................. G01C 22/006 702/141 |
| 2002/0022516 A1 | 2/2002 | Forden |
| 2002/0080035 A1 | 6/2002 | Youdenko |
| 2002/0082065 A1 | 6/2002 | Fogel et al. |
| 2002/0082077 A1 | 6/2002 | Johnson et al. |
| 2002/0090985 A1 | 7/2002 | Tochner et al. |
| 2002/0151992 A1 | 10/2002 | Hoffberg et al. |
| 2002/0160883 A1 | 10/2002 | Dugan |
| 2002/0163495 A1 | 11/2002 | Doynov |
| 2003/0103414 A1 * | 6/2003 | Lyon .................. G04G 17/083 368/10 |
| 2003/0208110 A1 * | 11/2003 | Mault .................. A61B 5/0002 600/300 |
| 2003/0224337 A1 | 12/2003 | Shum et al. |
| 2004/0023761 A1 | 2/2004 | Emery |
| 2004/0053690 A1 | 3/2004 | Fogel et al. |
| 2005/0068169 A1 * | 3/2005 | Copley .............. G08B 21/0283 340/539.13 |
| 2005/0101845 A1 | 5/2005 | Nihtila |
| 2005/0130802 A1 | 6/2005 | Kinnunen |
| 2005/0172311 A1 * | 8/2005 | Hjelt .................. A61B 5/1112 725/10 |
| 2005/0177051 A1 | 8/2005 | Almen |
| 2005/0275541 A1 | 12/2005 | Sengupta et al. |
| 2006/0025282 A1 | 2/2006 | Redmann |
| 2006/0031102 A1 | 2/2006 | Teller et al. |

(56) References Cited

U.S. PATENT DOCUMENTS

| | | | |
|---|---|---|---|
| 2006/0047447 A1* | 3/2006 | Brady | A63B 71/0605 |
| | | | 702/41 |
| 2006/0089538 A1 | 4/2006 | Cuddihy | |
| 2006/0089543 A1 | 4/2006 | Kim et al. | |
| 2006/0100530 A1* | 5/2006 | Kliot | A61B 5/0002 |
| | | | 600/483 |
| 2006/0122474 A1* | 6/2006 | Teller | A61B 5/02055 |
| | | | 600/300 |
| 2006/0141431 A1* | 6/2006 | Lee | A63F 13/12 |
| | | | 434/236 |
| 2006/0224051 A1 | 10/2006 | Teller et al. | |
| 2006/0264730 A1 | 11/2006 | Stivoric et al. | |
| 2006/0281543 A1 | 12/2006 | Sutton et al. | |
| 2006/0288781 A1 | 12/2006 | Daumer | |
| 2007/0004482 A1 | 1/2007 | Ando et al. | |
| 2007/0038038 A1 | 2/2007 | Stivoric et al. | |
| 2007/0050715 A1* | 3/2007 | Behar | A61B 5/0002 |
| | | | 715/706 |
| 2007/0053513 A1 | 3/2007 | Hoffberg | |
| 2007/0111858 A1 | 5/2007 | Dugan | |
| 2007/0167204 A1 | 7/2007 | Lyle et al. | |
| 2007/0173705 A1 | 7/2007 | Teller et al. | |
| 2007/0177770 A1* | 8/2007 | Derchak | G06K 9/00496 |
| | | | 382/115 |
| 2007/0197274 A1 | 8/2007 | Dugan | |
| 2007/0208233 A1 | 9/2007 | Kovacs | |
| 2007/0208544 A1* | 9/2007 | Kulach | A61B 5/1112 |
| | | | 702/189 |
| 2007/0260482 A1 | 11/2007 | Nurmela et al. | |
| 2008/0027337 A1 | 1/2008 | Dugan et al. | |
| 2008/0094226 A1 | 4/2008 | O'Shea et al. | |
| 2008/0129518 A1 | 6/2008 | Carlton-Foss | |
| 2008/0146892 A1 | 6/2008 | LeBoeuf et al. | |
| 2008/0167535 A1 | 7/2008 | Stivoric et al. | |
| 2008/0167861 A1* | 7/2008 | Inoue | A61B 5/16 |
| | | | 704/206 |
| 2008/0182724 A1* | 7/2008 | Guthrie | A61B 5/1118 |
| | | | 482/8 |
| 2008/0191864 A1 | 8/2008 | Wolfson | |
| 2008/0218310 A1 | 9/2008 | Alten et al. | |
| 2008/0281633 A1* | 11/2008 | Burdea | A61B 5/0002 |
| | | | 705/2 |
| 2008/0318679 A1 | 12/2008 | Tran et al. | |
| 2009/0005140 A1 | 1/2009 | Rose et al. | |
| 2009/0121894 A1 | 5/2009 | Wilson et al. | |
| 2009/0270743 A1 | 10/2009 | Dugan et al. | |
| 2010/0033303 A1 | 2/2010 | Dugan et al. | |
| 2010/0160041 A1 | 6/2010 | Grant et al. | |
| 2010/0217096 A1* | 8/2010 | Nanikashvili | A61B 5/02438 |
| | | | 600/301 |
| 2010/0240458 A1 | 9/2010 | Gaiba et al. | |
| 2010/0287011 A1 | 11/2010 | Muchkaev | |
| 2011/0065504 A1 | 3/2011 | Dugan et al. | |
| 2011/0082008 A1 | 4/2011 | Cheung et al. | |
| 2011/0152367 A1 | 6/2011 | Artico | |
| 2011/0190055 A1 | 8/2011 | Leyvand et al. | |
| 2011/0260830 A1* | 10/2011 | Weising | G06F 3/015 |
| | | | 340/5.52 |
| 2011/0275483 A1 | 11/2011 | Dugan et al. | |
| 2012/0208676 A1 | 8/2012 | Shum et al. | |
| 2012/0252580 A1 | 10/2012 | Dugan | |
| 2012/0253487 A1 | 10/2012 | Dugan | |
| 2012/0253489 A1 | 10/2012 | Dugan | |
| 2012/0306643 A1 | 12/2012 | Dugan | |
| 2013/0006736 A1 | 1/2013 | Bethke et al. | |
| 2013/0252731 A1 | 9/2013 | Dugan et al. | |
| 2014/0011640 A1 | 1/2014 | Dugan | |
| 2015/0151198 A1 | 6/2015 | Dugan et al. | |
| 2017/0239578 A1 | 8/2017 | Dugan et al. | |

FOREIGN PATENT DOCUMENTS

| | | |
|---|---|---|
| EP | 1 292 218 B1 | 4/2006 |
| EP | 1 702 560 A1 | 9/2006 |
| EP | 1 743 571 A2 | 1/2007 |
| JP | 08103568 | 4/1996 |
| WO | WO 96/05766 A1 | 2/1996 |
| WO | WO 01/96986 A2 | 12/2001 |
| WO | WO 02/00111 A1 | 1/2002 |
| WO | WO 02/078538 A2 | 10/2002 |
| WO | WO 03/015005 A2 | 2/2003 |
| WO | WO 2004/019172 A2 | 3/2004 |
| WO | WO 2004/032715 A2 | 4/2004 |
| WO | WO 2004/034221 A2 | 4/2004 |
| WO | WO 2005/016124 A2 | 2/2005 |
| WO | WO 2005/027720 A2 | 3/2005 |
| WO | WO 2005/029242 A2 | 3/2005 |
| WO | WO 2005/092177 A1 | 10/2005 |

OTHER PUBLICATIONS

"Bluetooth." Wikipedia: The Free Encyclopedia. Aug. 10, 2009 <http://en.wikipedia.org/wiki/Bluetooth>.

Ichinoseki-sekine et al., "Improving the Accuracy of Pedometer Used by the Elderly with the FFT Algorithm," Medicine & Science in Sports & Exercise 2006,1674-1681.

Mann, W. et al., "Smart Phones for the Elders: Boosting the Intelligence of Smart Homes," Am. Assoc. for Artificial Intell., (AAAI ), Jul. 2002.

Office Action of U.S. Appl. No. 12/426,193 dated Jul. 27, 2012.

Jan. 28, 2013 Reply to Jul. 27, 2012 Office Action of U.S. Appl. No. 12/426,193.

Final Office Action of U.S. Appl. No. 12/426,193 dated Feb. 11, 2013.

Amendment Submitted with RCE of U.S. Appl. No. 12/426,193, filed Jul. 11, 2013.

Office Action of U.S. Appl. No. 12/538,862 dated Nov. 17, 2011.

May 17, 2012 Response to Office Action of U.S. Appl. No. 12/538,862.

Final Office Action of U.S. Appl. No. 12/538,862 dated Jul. 31, 2012.

Amendment Submitted with RCE of U.S. Appl. No. 12/538,862, filed Jul. 1, 2013.

Interview Summary of U.S. Appl. No. 12/538,862, filed Aug. 8, 2013.

Examiner Interview Summary of U.S. Appl. No. 12/538,862 dated Aug. 27, 2013.

Office Action of U.S. Appl. No. 12/538,862 dated Apr. 28, 2014.

Office Action of U.S. Appl. No. 12/426,193 dated Jun. 30, 2014.

Jovanov et al., "A wireless body area network of intelligent motion sensors for computer assisted physical rehabilitation," Journal of NeuroEngineering and Rehabilitation, 2005,2:6; pp. 1-10.

Aug. 28, 2014 Reply to Apr. 28, 2014 Office Action of U.S. Appl. No. 12/538,862.

Examiner Interview Summary of U.S. Appl. No. 12/426,193 dated Sep. 15, 2014.

Notice of Allowance & Examiner Interview Summary of U.S. Appl. No. 12/538,862 dated Oct. 28, 2014.

Notice of Abandonment of U.S. Appl. No. 12/426,193 dated Jan. 16, 2015.

Non-Final Office Action of U.S. Appl. No. 14/619,061, dated Jul. 31, 2015.

Dec. 31, 2015 Reply to Jul. 31, 2015 Non-Final Office Action of U.S. Appl. No. 14/619,061.

Final Office Action of U.S. Appl. No. 14/619,061, dated May 5, 2016.

Amendment Submitted with RCE of U.S. Appl. No. 14/619,061, filed Nov. 7, 2016.

Notice of Allowance of U.S. Appl. No. 14/619,061, dated Jan. 20, 2017.

Amendment After Allowance of U.S. Appl. No. 14/619,061, filed Apr. 19, 2017.

(56) References Cited

OTHER PUBLICATIONS

Comments on Reason for Allowance of U.S. Appl. No. 14/619,061, fled Apr. 20, 2017.
Corrected Notice of Allowability, Response to Rule 312 Communication and Examiner-Initiated Interview Summary of U.S. Appl. No. 14/619,061 dated May 5, 2017.
Non-Final Office Action of U.S. Appl. No. 15/591,084 dated Jul. 13, 2017.
Dec. 13, 2017 Reply to Jul. 13, 2017 Non-Final Office Action of U.S. Appl. No. 15/591,084.
Notice of Allowance of U.S. Appl. No. 15/591,084 dated May 10, 2018.
Amendment After Allowance of U.S. Appl. No. 15/591,084, filed Aug. 10, 2018.
Response to Rule 312 Communication of U.S. Appl. No. 15/591,084 dated Aug. 27, 2018.
Corrected Notice of Allowability of U.S. Appl. No. 15/591,084 dated Sep. 21, 2018.

* cited by examiner

SYSTEMS AND METHODS FOR PROVIDING BIOFEEDBACK INFORMATION TO A CELLULAR TELEPHONE AND FOR USING SUCH INFORMATION

RELATED APPLICATIONS

This application is a continuation of and claims priority to U.S. patent application Ser. No. 15/591,084, filed May 9, 2017, and titled "SYSTEMS AND METHODS FOR PROVIDING BIOFEEDBACK INFORMATION TO A CELLULAR TELEPHONE AND FOR USING SUCH INFORMATION", which is a continuation of and claims priority to U.S. patent application Ser. No. 14/619,061, filed Feb. 10, 2015, and titled "SYSTEMS AND METHODS FOR PROVIDING BIOFEEDBACK INFORMATION TO A CELLULAR TELEPHONE AND FOR USING SUCH INFORMATION", now U.S. Pat. No. 9,675,875, which is a continuation of and claims priority to U.S. patent application Ser. No. 12/538,862, filed Aug. 10, 2009, and titled "SYSTEMS AND METHODS FOR PROVIDING BIOFEEDBACK INFORMATION TO A CELLULAR TELEPHONE AND FOR USING SUCH INFORMATION", now U.S. Pat. No. 8,976,007, which claims priority to U.S. Provisional Patent Application No. 61/087,698, filed Aug. 9, 2008 and entitled "SYSTEMS AND METHODS FOR PROVIDING BIOFEEDBACK INFORMATION TO A CELLULAR TELEPHONE AND FOR USING SUCH INFORMATION" and which is a continuation-in-part of and claims priority to U.S. patent application Ser. No. 12/426,193, filed Apr. 17, 2009 and entitled "SYSTEMS AND METHODS FOR PROVIDING AUTHENTICATED BIOFEEDBACK INFORMATION TO A MOBILE DEVICE AND FOR USING SUCH INFORMATION", which claims priority to U.S. Provisional Patent Application No. 61/045,955, filed Apr. 17, 2008. All of the above applications are hereby incorporated by reference herein in their entirety.

FIELD OF THE INVENTION

The present invention relates to the use of biofeedback devices, and more particularly to systems and methods for providing authenticated biofeedback information to a mobile device such as a cellular telephone and for using such information.

BACKGROUND

Biofeedback devices such as portable heart rate monitoring (HRM) devices are commonly used in fitness related activities for weight loss, goal heart rate (HR) training, and general HR monitoring. Such devices may sometimes be employed by healthcare professionals for chronic and/or acute heart condition monitoring and/or diagnosis.

Portable HRMs and other monitoring devices typically are expensive, and in some cases are cost prohibitive for many consumers. A need exists for inexpensive and/or simplified monitoring systems.

SUMMARY

In some embodiments, the present invention provides a wearable band adapted to be worn by a user. The wearable band includes a pulse monitor adapted to monitor a pulse of the user at the user's wrist; and a transmitter adapted to wirelessly transmit pulse information from the pulse monitor to a cellular telephone. The wearable band does not include a display for the pulse information.

In some other embodiments, the present invention provides a system adapted to monitor biometric information of a user. The system includes a wearable band having a pulse monitor adapted to monitor a pulse of the user; and a transmitter adapted to wirelessly transmit pulse information from the pulse monitor to a cellular telephone. The wearable band does not include a display for the pulse information and the cellular telephone is adapted to receive the pulse information from the wearable band.

In still other embodiments, the present invention provides a system which includes a plurality of wearable bands, the wearable bands each including one or more accelerometers, an identification indicia, one or more proximity sensors, and a communications device; and a mobile device adapted to communicate with one or more of the plurality of wearable bands and to determine an activity of a wearer of the plurality of wearable bands based on information transmitted by the wearable bands.

DETAILED DESCRIPTION

Figure 1:
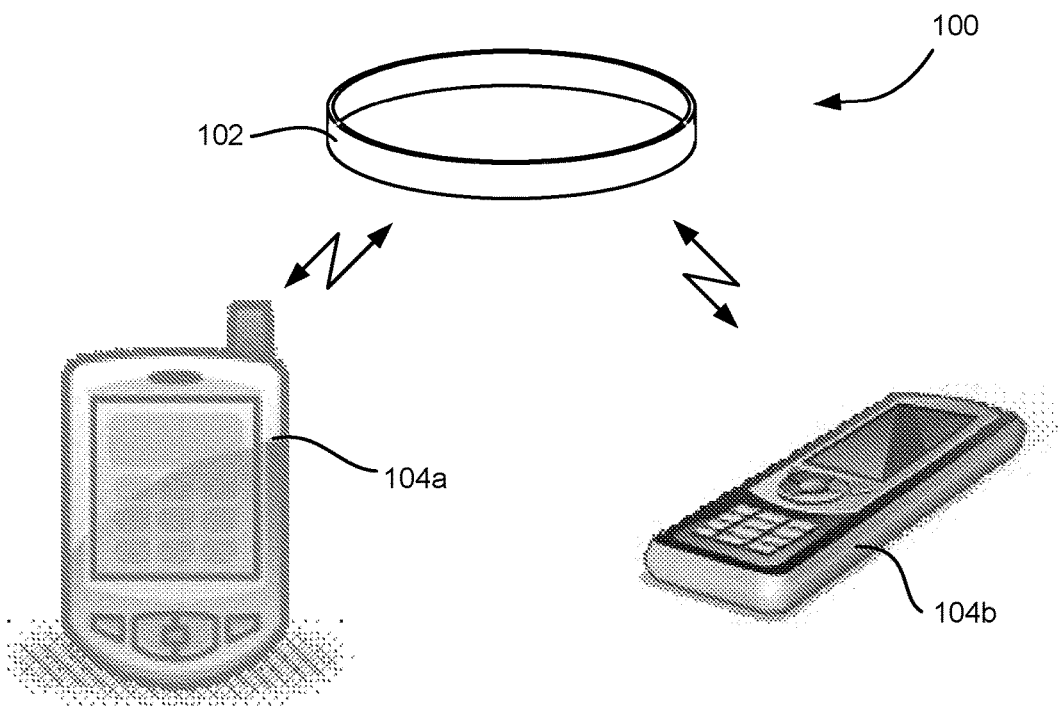
FIG. 1 is a schematic diagram of an exemplary system for sensing, collecting and/or monitoring biometric information from a user according to some embodiments of the present invention.

In one or more embodiments of the invention, wearable monitors and/or sensors are provided which may communicate wirelessly with a mobile device such as a cellular telephone, personal digital assistant or other portable computing device. For example, a wrist, ankle or other body part band, strap, bracelet or other securing mechanism may include one or more monitors or sensors adapted to sense biometric information from a user and to transmit this information to a cellular telephone, personal digital assistant or other portable device. Exemplary biometric information that may be monitored includes, but is not limited to, heart rate, pulse rate, temperature, respiration, acceleration, skin resistivity, etc.

In some embodiments, a band or bracelet may be provided for each arm and/or each ankle of a user to monitor arm and leg position during golf, tennis, running, etc., and to provide this or other biometric information to a cellular telephone, personal digital assistant or other portable device. Such a system may be used, for example, to determine stride length during running, body position during a golf or tennis swing, "hang time" during a basketball dunk, and the like.

In one or more embodiments, an accelerometer may be provided within a band or bracelet. The accelerometer may be employed to measure acceleration during a golf, tennis, hockey, or other swing. Such acceleration information may be wirelessly transmitted to a cellular telephone, personal digital assistant or other portable device and used to determine club, racquet or stick speed, club, racquet or stick velocity, swing tempo, or the like. In some embodiments, such acceleration information may be adjusted to compensate for the affects of gravity. Software and/or one or more computer program products on the cellular telephone or other portable device may be employed to calculate or otherwise determine any relevant information.

For example, in a golf embodiment, the portable device may employ the acceleration information from a band or bracelet to determine (1) acceleration of a club during a swing (e.g., club head acceleration); (2) velocity and/or speed of a club during a swing (3) swing tempo; (4) ball-club contact; (5) ball-club contact force; (6) ball-club contact timing; (7) follow through speed, timing and/or tempo; (8) number of strokes of a golf club and/or golfer; (9) predicted ball travel distance (e.g., based on ball-club contact force, club type, swing speed, etc.); (10) predicted ball position (e.g., based on ball-club contact force, club type, swing speed, etc.); (11) golf score; (12) golf handicap; and/or any other similar information.

In another exemplary embodiment, an accelerometer or other sensor may be used to monitor acceleration and/or striking force during a boxing or mixed martial arts (MMA) event (e.g., by embedding the accelerometer in a band or glove worn by a participant) and to provide this or other biometric information to a cellular telephone, personal digital assistant or other portable device.

The present invention also aggregates various inputs from one or more sensors (e.g., in the wearable bands) and provides messages (e.g., signals) to a central system (e.g., a game console, a mobile device running a game program, etc.) indicating sensed "macro" status information (e.g., compound activities/statuses) about a user and/or the user's activity or experiences. In other words, based on verifiable data collected/acquired and aggregated from one or more sensors, the present invention provides an authenticated or verified indication that a user is taking an action or experiencing a particular sensation or physical, physiological, or mental "occurrence." This authenticated information may then be used to impact, alter, and/or adjust the central system (e.g., change game play on a game console). For example, a video game that wants to require that the user is maximally exerting himself may rely upon an authenticated message from the apparatus of the present invention that confirms the user's maximal exertion. Thus the video game does not have to evaluate or even be aware of the whole array of parameters and corresponding raw data collected from various sensors (e.g., in the wearable bands) such as the user's heart rate (e.g., from an HRM) being above a certain percentage threshold, user perspiration level (e.g., from a moisture sensor) being above a certain threshold, user body temperature level (e.g., from a thermometer) being above a certain threshold, user impact shock level (e.g., from an accelerometer) being above a certain threshold, user acceleration/deceleration (e.g., from an accelerometer) being above a certain threshold, user motion frequency (e.g., from accelerometer(s) and/or proximity sensor(s)) being above a certain threshold, user speed of movement (e.g., from a GPS and clock) being above a certain threshold, user breathing frequency being above a certain threshold (e.g., from a microphone, HRM, etc.), user breathing depth level (e.g., from a microphone, HRM, etc.) being above a certain threshold, user muscle flexing frequency (e.g., from accelerometer(s) and/or proximity sensor(s)) being above a certain threshold, user blood pressure (e.g., from a blood pressure monitor) being above a certain threshold, user pulse oxygen level (e.g., from a pulse oxygen monitor) being above a certain threshold, user blood sugar or insulin or cholesterol levels being above or below certain thresholds (e.g., from an automated blood tester), user muscle expansion (e.g., from a measurement of the muscle size), etc. In other words, the present invention defines a protocol and an interface for providing authenticated activity or status information about a user based on an aggregation of sensed data.

FIG. 1 is a schematic diagram of an exemplary system 100 for sensing, collecting and/or monitoring biometric information from a user (not shown). The system 100 includes a wearable band 102 having one or more monitors or sensors (not shown) adapted to monitor or otherwise sense, for example, heart rate, pulse rate, temperature, respiration, acceleration, skin resistivity, or any other biometric information. The wearable band 102 may (wirelessly) transmit the biometric information to one or more cellular telephones 104a-b or other portable devices such as personal digital assistants, MP3 players, portable video game players, or the like. While two cellular telephones are shown in FIG. 1, it will be understood that any number of portable devices (e.g., 1, 2, 3, 4, 5, etc.), differing types of portable devices, etc., may receive biometric information from the band 102.

Each cellular telephone 104a-b, or any other portable device receiving information from the band 102, may be programmed to process the biometric information received from the band 102 (e.g., for general health monitoring, determining swing information, monitoring sleep patterns, enhancing video game performance by affecting a video game character or characteristic based on the biometric information, etc.).

In some embodiments, the band 102 may be flexible, continuous and/or water resistant.

Figure 2:
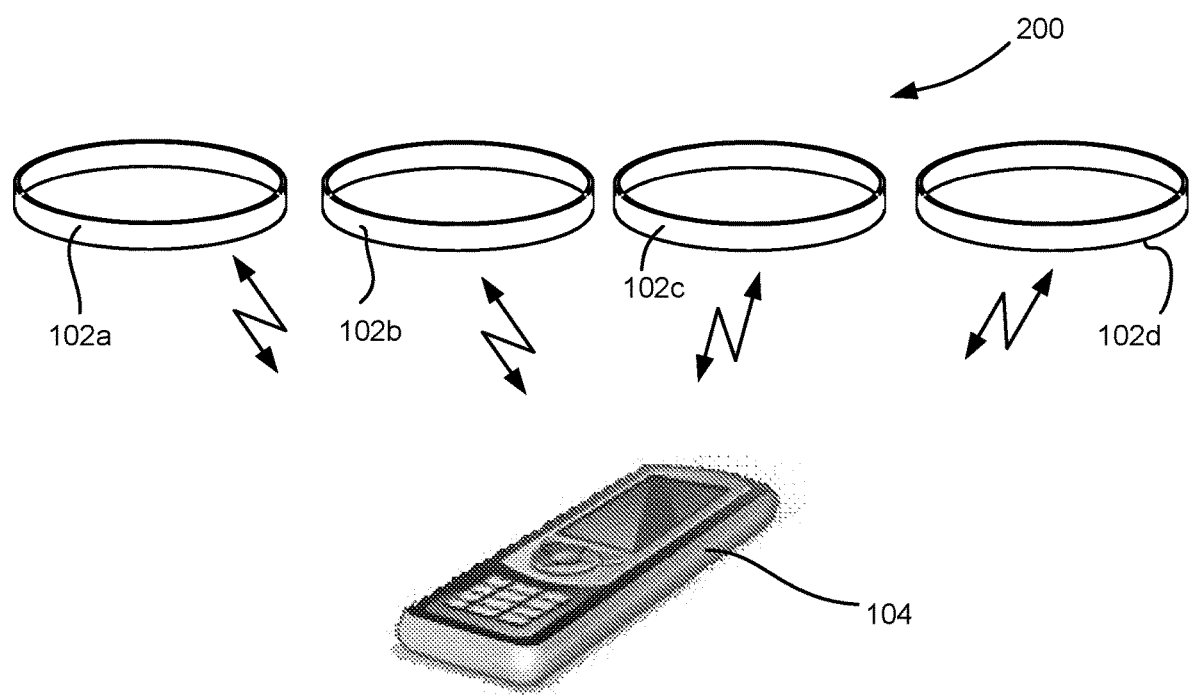
FIG. 2 is a schematic diagram of an alternative exemplary system for sensing, collecting and/or monitoring biometric information from a user according to some embodiments of the present invention.

FIG. 2 is a schematic diagram of an alternative system 200 for sensing, collecting and/or monitoring biometric information from a user (not shown). In the embodiment of FIG. 2, four bands 102a-d communicate information to a cellular telephone 104 (or other portable device). For example, a user may employ a band 102 on each arm and each ankle, or multiple users may employ a band 102. Other numbers of bands and/or portable devices may be used.

Figure 3:
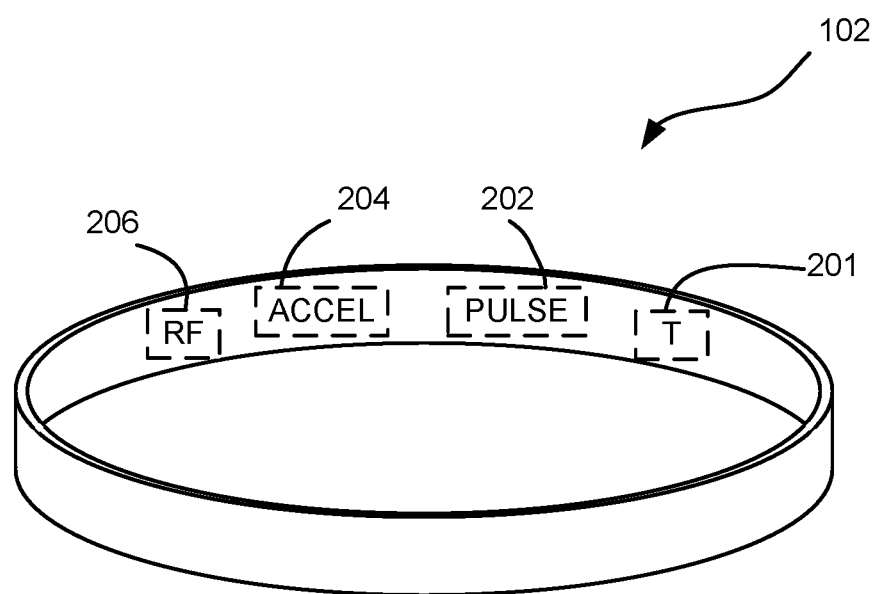
FIG. 3 is a side perspective view of an exemplary wearable band provided in accordance with some embodiments of the invention.

FIG. 3 is a side perspective view of an exemplary band 102 provided in accordance with the invention. In the embodiment shown, the band 102 includes a temperature sensor 201, a pulse monitor 202, an accelerometer 204 and an RF transmitter 206 for wirelessly transmitting information from each monitor/sensor 200-204 to a cellular telephone, mobile device/HCD or other portable device. In some embodiments, each monitor/sensor 201-204 is embedded in the band 102 so as to be protected, such as from moisture (e.g., sweat, water, rain, snow, etc.). Other numbers and/or types of monitors/sensors may be used. Any suitable communication protocol may be used to transmit information between the band 102 and a portable device (e.g., Bluetooth, WiFi, RF, optical, etc.).

In some embodiments, a cellular telephone or other portable device may be employed to display exercise information for a user during exercise. For example, a stepper, elliptical or other piece of exercise equipment may include a crude or rudimentary display of calories burned, steps taken, miles walked, pulse rate, etc. A cellular telephone, portable video game device, personal digital assistant, etc., receiving information from a band, bracelet, strap or the like may provide a much more enjoyable and interactive interface, for example, displaying an avatar representation of an exerciser, a mountain or hill or any other environment for the exerciser to climb or pass through, exercise statistics, graphs of exercise level and/or performance, etc.

In some embodiments, for example using multiple bands, the bands may operate as a mobile ad hoc and/or mesh network to allow the bands to communicate with each other and collectively provide relative positioning information using information derived from, for example, built-in accelerometers, GPS sensors, identification signals, proximity sensors (e.g., sensors that determine distance from other bands based on, e.g., received signal relative strength), etc. The relative positioning information may be used to deduce the activity or position of the wearer or wearers of the bands. For example, if four bands worn on the four appendages of a single user collectively determine and report (e.g., via a wireless signal to a mobile device) that they are all within approximately 10 cm of each other, the mobile device receiving the signal may determine that the user is touching his toes. If within, for example, approximately 10 seconds, the signal is preceded by a prior signal from the bands worn on the user's ankles that the ankle bands are less than approximately 10 cm apart from each other but both the wrist bands are greater than approximately 40 cm from the ankle bands, the mobile device may deduce that the user has just bent over to touch his toes.

As indicated above, in addition to proximity sensors, accelerometers in the bands may be used to sense and report data that corroborates the deduction that the user has bent over. In addition to corroborating the user's body motion, the accelerometers may also be used to determine the orientation of the user's body before, after, and/or at the time of the motion so that, for example, it may be determined that the user is touching his toes while seated versus toe touching while standing. Further, a fifth band (or strap or sensor e.g., included in the mobile device) may be worn on the user's torso and allow the system to determine for example, whether the user's arms and/or legs are extending (e.g., stretched) during the toe touch or retracted (e.g., in an "Indian-style" position) during the toe touch.

In some embodiments, the body position and user activity information that may be deduced by the system of wearable bands and mobile device described above, may be further enhanced by incorporating other sensed biometric information such as, e.g., heart rate, body temperature, and identification (e.g., voice identification) information. For example, heart rate information detected and transmitted by the wearable bands may be used to deduce that the user is engaging in strenuous activity and combined with, e.g., corroborating body positioning and orientation information as well as identity information (e.g., a recorded response to a voice prompt from the mobile device, a user specific heart rhythm pattern, etc.), the system can reliably deduce that the particular user is, e.g., performing a particular exercise or has achieve a particular body status, e.g., physical exhaustion.

In one or more embodiments of the invention, a flight simulator video game may be provided on a cellular telephone (and/or other mobile device, e.g., any number of handheld computing devices (HCDs) including cellular or other telephones) and biometric data from one or more of the wearable bands (or other measurement/sensor devices) may be used to affect the flight simulator video game. For example, for a plane to take off or land safely from an airstrip in the game, a user may be required to have a relatively rapid pulse or heart rate (e.g., 130 plus pulses/minute). In this manner, a user may have to pedal, run, row, walk or otherwise exercise harder to take-off or land a plane in the video game. Thereafter, the user may be required to maintain a predetermined pulse or heart rate in order keep the plane in flight. The longer the user exercises, the longer and/or better the user does at the video game (e.g., by keeping the plane airborne). Some cellular telephones/HCDs, such as, for example, an iPhone available from Apple, Inc., of Cupertino, Calif., include one or more accelerometers for measuring the orientation of the cellular telephone (for affecting display size and orientation). In some embodiments of the invention, such accelerometers may be used as part of the flight simulator to control position (e.g., level, climbing, lowering) of the plane. In other embodiments, external accelerometers or other sensors, such as in one or more wearable bands, may measure arm and/or leg position and/or orientation and provide such information to the cellular telephone. The cellular telephone may then use this position and/or orientation information to control position of the plane. For example, a game player may be required to wear two wrist bands and two ankle bands, each with accelerometers or other position and/or orientation sensors. Movement of the game player's arms and legs may be used to control movement of the plane. For example, a game player may be required to lay on his or her back and raise his or her legs together to have a plane climb, lower his or her legs together to have the plane dive, raise one leg only to have the plane bank right, raise the other leg only to have the plane bank left, or the like. Similar or other plane movements may be controlled by arm position and/or orientation. Note that such a video game embodiment may be performed on a non-mobile or non-portable video game platform (e.g., a Microsoft® xBox, Sony® Playstation®, Nintendo® Wii™, etc.).

In another embodiment, an MMA or similar fight-based video game may be provided on a cellular telephone/HCD and biometric data from one or more of the wearable bands or other measurement devices may be used to affect the fight-based video game. For example, a video game player may be required to wear two wrist bands and two ankle bands, each with accelerometers or other position and/or orientation sensors. Movement of the game player's arms and legs may be used to control movement of a video game player (e.g., blocking, striking, kicking, kneeing, throwing, jumping, etc.). The difference between blocking and striking (or kicking) may be determined based on, for example, movement of an arm or wrist band toward the cellular telephone (e.g., using multi-axis accelerometers or other multi-axis sensors). Such a system may additionally or alternatively be used to teach self defense and/or Martial arts, or other exercise activities, such as Kung Fu, Tae Kwon Do, Muay Thai Boxing, Tai Chi, Pilates, Yoga, Dance or the like by providing a user real time feedback about proper and improper body position and/or orientation. For example, biometric readings from multiple acceleration and/or other monitors coupled to a user may be correlated with body position and/or orientation (e.g., arm, leg, torso, hip, head or other body part position, relative position and/or orientation) and then used during a video game or instruction lesson. Note that such a video game embodiment may be performed on a non-mobile or non-portable video game platform (e.g., a Microsoft® xBox, Sony® Playstation®, Nintendo® Wii™, etc.).

In some other embodiments, a user may employ one or more wearable bands and/or other biometric sensors in combination with a cellular telephone/HCD or other similar device to collect biometric information during a predetermined time period (e.g., during all or part of a work day, daily, weekly, monthly, etc.) and then employ this information to affect video game play. For example, a user may wear a band (e.g., a wrist band) that measures and transmits pulse or heart rate information to a cellular telephone during the course of a work day. Other information may be collected such as calories consumed. At the end of the work day, the user may analyze the collected data to determine one or more of periods of high stress, calories burned, etc., and/or may use the information to affect video game play (e.g., such as on a train ride back from the office). The cellular phone may also employ this information to determine (1) recommended food choices based on calories consumed or burned, types of food already eaten, etc.; (2) additional types or amounts of exercise the user should perform; or (3) the like.

Any of the above or alternative embodiments may be used alone or in combination to provide "fitness-enhanced" entertainment.

In some embodiments, the system may include a calibration function that allows the user to provide examples to the system of the way the user performs/achieves particular activities, body positions/orientations, and body status information. For example, the mobile device/HCD may instruct the user to lie still for ten second, jog in place for ten seconds, perform ten "jumping jack" exercises, perform ten "squat-thrust" exercises, and then lie still again for ten seconds. While the user executes the five different exercises/activities under the direction of the mobile device (e.g., via voice commands from the mobile device), the system may sense and record data that will allow the system to reliably recognize similar body positions, activities, and body status as well as combinations of data that indicate other body positions, activities, and body status. Along with activities that the system actually "observes" (e.g., senses and records) during normal activity, the example data captured during the calibration function (e.g., during directed resting, jogging, jumping jacks, squat-thrusts, and post-exertion resting) may be used to build a database (e.g., stored on the mobile device) of activities, body positions/orientations, and body status correlated to sensed data so that particular activities (and sequences of activities) may be quickly and reliably be identified. For example, in embodiments where the system includes a GPS and a clock, the activities, status, and locations of a user may be logged throughout a full day or over a period of weeks or years.

In some embodiments, the system may include an authentication function that uses various pieces of sensed information to corroborate the actual performance of activities, body positions/orientations/locations/identity, and body status of the user and to provide a signal that reliable indicates that a particular user has in fact, e.g., performed an activity at a given time and place. The signal from this authentication function may be used and relied upon as proof, for example, that a user performed an exercise (e.g., ran 10 laps at a track in 20 minutes on Aug. 10, 2009) or engaged in an activity (e.g., loaded a truck with heavy items, drove 150 miles, and unloaded the truck all in four hours). For example, the combination of heart rate data indicating the exertions of user, voice identification data indicating the identity of the user, GPS data indicating the locations over time of the user, wearable band proximity and accelerometer data indicating the body position/motion of the user, may all be captured, stored and correlated to authenticate the user's actual performance of a specific activity or set of activities.

In some embodiments, the present invention may include a protocol (e.g., a software protocol implementable and executable on a mobile or other device, including a system in accordance with the present invention) for sensing, collecting, storing, authenticating, and securely reporting a user's actual performance of activities, body positions/orientations/locations/identity, and/or body status of the user. In addition the protocol may include a function (e.g., an application program interface (API)) for requesting authentication of a particular activity or body position/status. In other words, the present invention may include software (e.g., an authentication module) that allows, for example, another program (e.g., a video game application, a medical treatment program, a business workflow tracking program, etc.) to request and receive an indicia (e.g., a signal, an encrypted code, etc.) from the system of the present invention that reliably verifies that a user has engaged in a particular activity or achieved a particular body status. For example, the system 200 of the present invention may provide an interface to a game system (e.g., a video game console, a program running on the mobile device of the system itself, etc.) that (1) rewards the user with enhanced game features and/or (2) allows the user to control the game, based on performance of specific activities, body positions/orientations/locations/identity, and/or body status. The interface may include a set of predefined activities/statuses such that the game may request and receive verification of the activities/statuses by calling the function with any number of various pre-defined parameters such as an identifier of the particular activity/status of interest (e.g., activity ID), the time of the activity/status (e.g., timestamp), a degree of exertion associated with the activity/status (e.g., level, intensity), a rate associated with the activity/status (e.g., pace), an efficiency or performance rating associated with the activity/status, etc.

Further, in some embodiments the interface may provide the game with access to historical information regarding the activities/statuses of the user stored in a historical database. The database may include one or more fields that identify recognized or deduced activities of the user wearing the bands. The activities may be macro or compound activities/statuses that are aggregated combinations or sets of sub-activities and/or sensed data that together corroborate the performance of the compound activities/statues.

An example list of compound activities or macro status information that may be determined/deduced and authenticated using the systems and protocols of the present invention (e.g., an authentication module 406) includes determining that a user is maximally exerting himself (e.g., based on heart rate being greater than a percentage of the user's maximum heart rate, perspiration, body temperature, impact shock level/acceleration/de-acceleration, motion frequency, speed (delta GPS information), breath frequency, breath depth, muscle flexing, blood pressure, pulse oxygen level); user is sleeping; user is relaxed; user is moderately exerting; user is minimally exerting; user is dead; user is unconscious; user is intoxicated; user is in pain; user is in shock; user is experiencing a heart attack (fibrillation); user is aroused; user is experiencing a particular physical sensation or stimulation; user is conscious; user is awake; user is in free fall; user is dizzy; user is X % exhausted; user is at physical failure; user is hot/cold; user is dehydrated (e.g., based on electrical measurement of user's body relative water content); user blood sugar level is high/low (e.g., based on an automated blood test); user insulin level is high/low; user is hungry/thirsty; user is laughing; user is suffocating; user is asphyxiating (e.g., based on blood oxygen level measurement); user is overweight; user is out of shape; user is fit; user is under-weight; user is tense; user is nervous; user is angry; user is lying; user is being tickled; user is sneezing; user is depressed; user is happy; user is confused; user is afraid; user is running at X % maximum speed; user is walking at X % maximum speed; user is dancing; user is swimming; user is skipping; user is jumping; user is punching (with left/right) (jab/cross/hook/upper cut/8 point blocking); user is kicking (left/right) (front/side/round house/back); user is rowing; user is prone (front/back); user is kneeling/sitting/standing; user is throwing (left/right); user is balancing; user is dribbling a ball; user is cradling a lacrosse stick; user is cradling a baby; user is eating/drinking; user is crying; user is driving; user is swinging a bat/tennis racket/golf club/lacrosse stick; user is typing; user is thinking; user is talking, and the like. These activities may be stored in a database of activities 408 that associates each of the activities with stored patterns of biometric information.

Further, in some embodiments the interface may provide real time access to the current activities/statues of the user. For example, the system of the present invention may provide a stream of data reporting actual sensed data and/or recognized activities that are deduced from and corroborated by the sensed data. The stream of recognized activities delivered by the interface may be encoded or even encrypted so that the game (or other application requesting the information) can have a high degree of confidence that the activities/statuses are authentic. Thus, the game (or other application requesting the information) can reasonably decide to transfer value based on the authenticated information. For example, a valuable contest prize can be awarded to the winner of a game that relies on the protocol of the present invention to verify that the winner in fact performed the required activities to win the game. Likewise, an employer can allow a workflow program running on a host system to decide to pay an employee for performing a task (e.g., load and drive a truck) by using the systems and protocols of the present invention to verify timely and efficient performance of the task.

Figure 4:
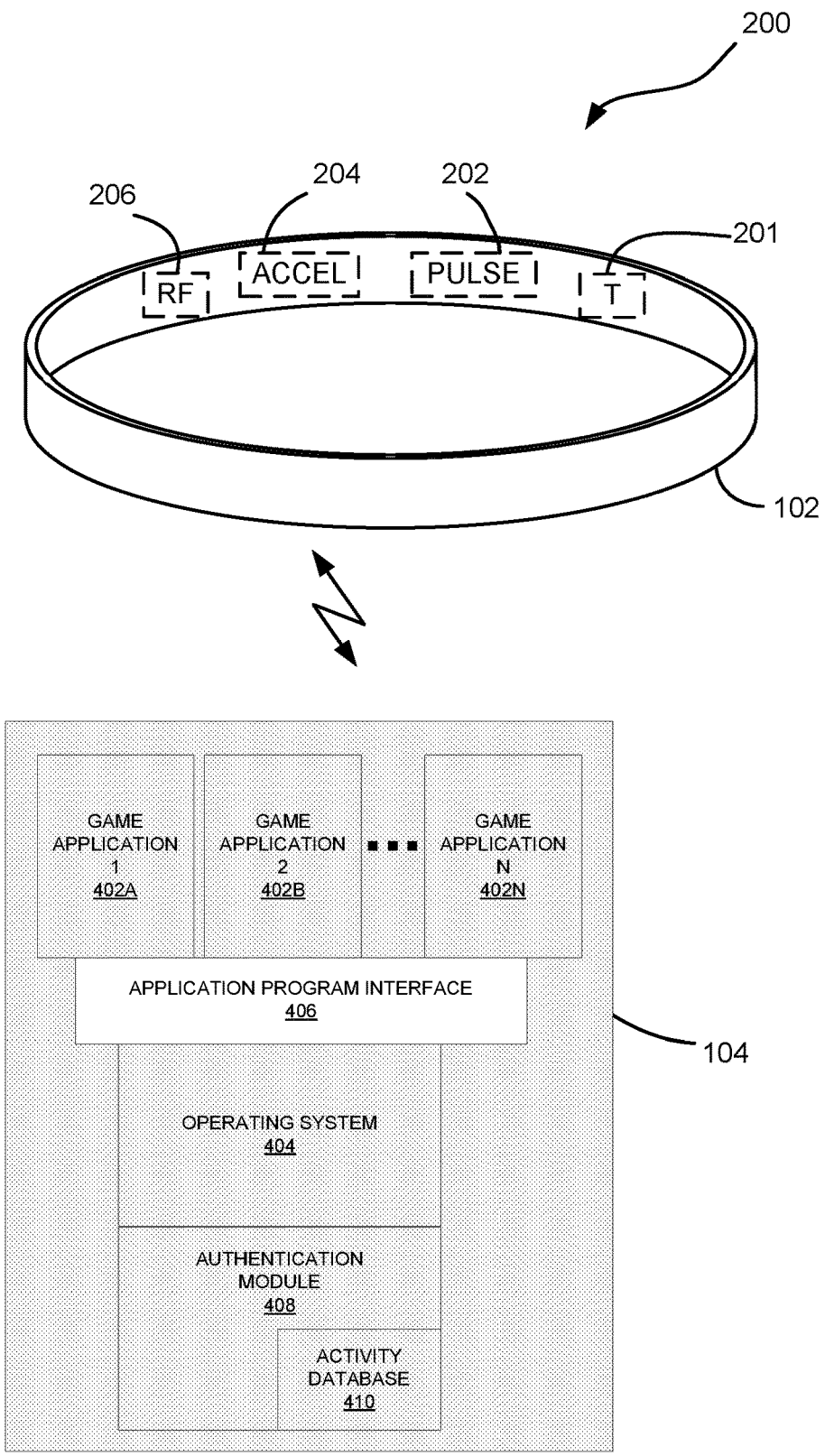
FIG. 4 is a block diagram depicting an example system according to some embodiments of the present invention.

Turning to FIG. 4, an example system 200 of the present invention is depicted. Any number of wearable bands 102 (only one pictured) or other sensors may be in communication (e.g., wirelessly) with one or more mobile devices/HCDs 104 (only one pictured). The wearable bands 102 may include the features 201, 202, 204, 206 as described above with respect to FIG. 3. The mobile device/HCD 104 may include any number of game applications 402A, 402B, 402N or other applications. The game applications 402A, 402B, 402N may run on an operating system 404 that general directs and controls basic functions of the mobile device/HCD 104. The mobile device/HCD 104 may also include an application program interface (API) 406 that allows game applications 402A, 402B, 402N to present requests and receive data from an authentication module 408 that includes an activity database 410. As described above, an authentication module 408 may provide authentication of a users activities to the game applications 402A, 402B, 402N via the API 406. In some embodiments the API 406 may include the authentication module 408 and/or the activity database 410 or other databases discussed above.

Figure 5:
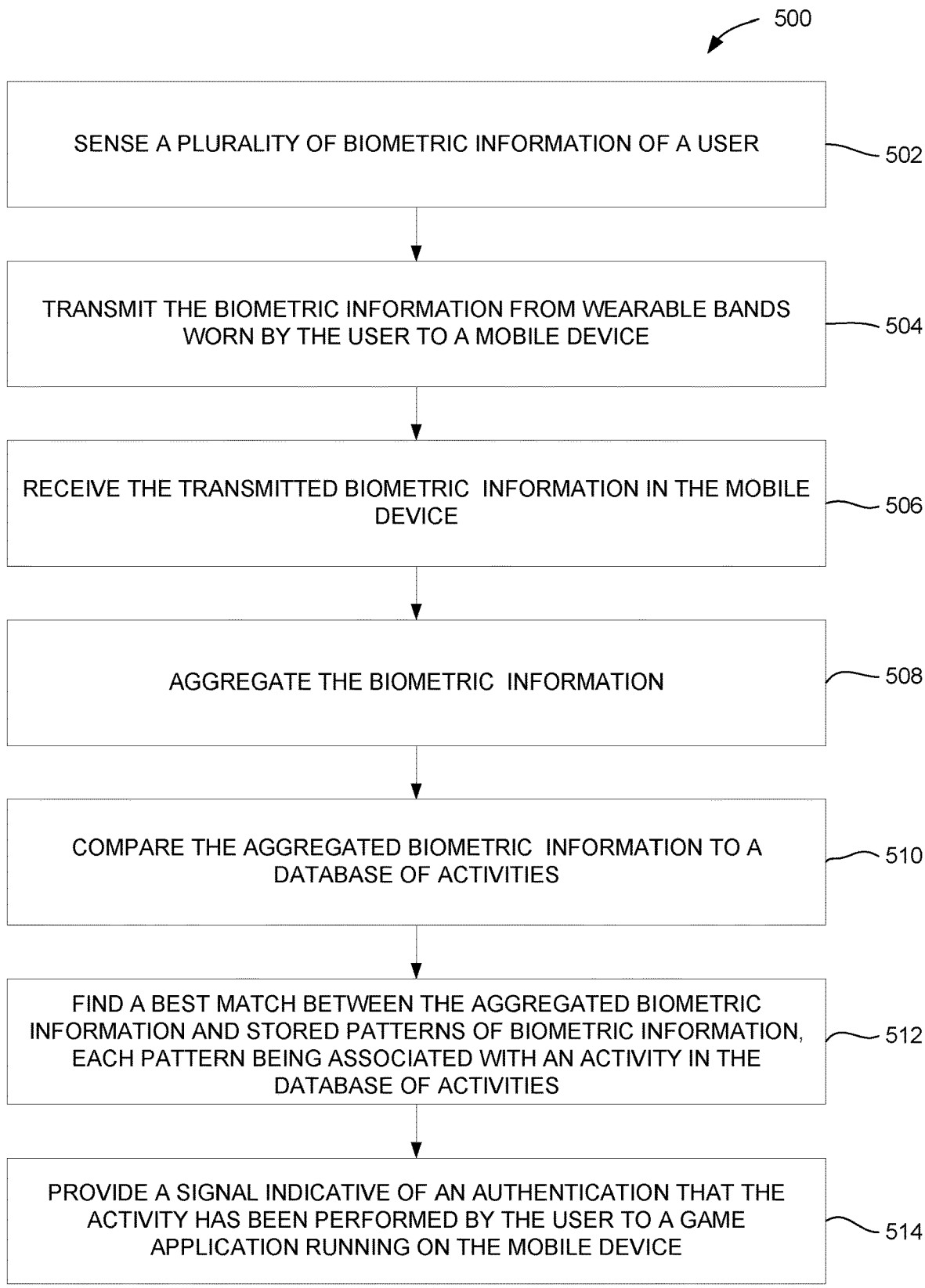
FIG. 5 is a flow chart depicting an example method according to some embodiments of the present invention.

Turning to FIG. 5, an example method 500 of the present invention is depicted as a flow chart. In step 502, a plurality of biometric information of a user is sensed. In step 504, the biometric information is transmitted from wearable bands worn by the user to a mobile device/HCD. In step 506, the transmitted information is received in the mobile device. In steps 508 to 512, an activity associated with the information is identified or determined. In step 508, the information is aggregated together. In step 510, the aggregated information is compared to a database of activities. In step 512, a best match between the aggregated information and stored patterns of information each associated with an activity in the database of activities is found. In step 514, a signal indicative of an authentication that the activity has been performed by the user is provided to a game application running on the mobile device.

Accordingly, while the present invention has been disclosed in connection with the exemplary embodiments thereof, it should be understood that other embodiments may fall within the spirit and scope of the invention, as defined by the following claims.

What is claimed is:

1. A system comprising:
a plurality of wearable bands, the wearable bands each including one or more accelerometers, and a communications device; and
an application executable on a mobile device adapted to communicate with one or more of the plurality of wearable bands and to determine an activity of a wearer of the plurality of wearable bands based on information transmitted by the wearable bands,
wherein the application executable on the mobile device is further operative to determine that the user has timely completed a task; and
wherein the application executable on the mobile device includes an authentication module and a workflow program, wherein the authentication module is operative to aggregate information transmitted by the wearable bands and provide authenticated activity information to the workflow program, and wherein the workflow program is operative to pay an employee wearing the bands based on the authenticated activity information.

2. The system of claim 1 wherein the accelerometers and communications device are internal to the bands.

3. The system of claim 1 wherein the authentication module includes a database of activities, and wherein the authentication module is operative to match aggregated information transmitted by the wearable bands to one or more activities in the database of activities and to select a best match from among the matched one or more activities.

4. The system of claim 1 wherein the application executable on the mobile device is operative to determine that the user is engaging in strenuous activity.

5. The system of claim 1 wherein the application executable on the mobile device is operative to determine that the user has achieved physical exhaustion.

6. The system of claim 1 wherein the application executable on the mobile device is operative to determine that the user has efficiently completed a task.

7. The system of claim 1 wherein the application executable on the mobile device is operative to determine that the user has driven a truck.

8. The system of claim 1 wherein the application executable on the mobile device is operative to determine that the user has loaded a truck.

9. The system of claim 1 further comprising a host system in communication with the mobile device and operative to decide the user should be paid for performing the activity and to pay the user.

10. A method comprising:
sensing a plurality of biometric information of a user wearing a plurality of wearable bands, the wearable bands each including one or more accelerometers, and a communications device;
communicating the biometric information from the wearable bands worn by the user to a mobile device; and
determining by an application executable on the mobile device an activity of the user based on the biometric information, wherein determining an activity of the user includes aggregating the biometric information and comparing the aggregated biometric information to a database of activities, providing a signal indicative of an authentication that the activity has been performed by the user to a workflow program executing on the mobile device wherein the authentication is based on a best match of the aggregated biometric information transmitted by the wearable bands with an activity in the database of activities; and paying the user for work performed based on the signal.

11. The method of claim 10 wherein determining an activity of the user further includes finding a best match between the aggregated biometric information and stored patterns of information each associated with an activity in the database of activities.

12. The method of claim 10 wherein determining an activity of the user includes at least one of determining that the user is engaging in strenuous activity, determining the user has achieved physical exhaustion, determining that the user has timely completed a task, determining that the user has efficiently completed a task, determining that the user has driven a truck, and determining that the user has loaded a truck.

13. The method of claim 10 wherein paying the user for work performed based on the signal includes a host system deciding the user should be paid for performing the activity.

14. The method of claim 13 wherein paying the user for work performed based on the signal includes the host system paying the user.

15. A system comprising:
a wearable band, the wearable band including one or more accelerometers and a communications device, wherein the accelerometers and communications device are internal to the wearable band; and
an application executable on a mobile device adapted to communicate with the wearable band and to determine an activity of a user of the wearable band based on information transmitted by the wearable band,
wherein the application executable on the mobile device includes an authentication module and a workflow program, wherein the authentication module is operative to aggregate the information and provide authenticated activity information to the workflow program, and wherein the workflow program is operative to pay the user wearing the band based on the authenticated activity information.

16. A system comprising:
a plurality of wearable bands, the wearable bands each including one or more accelerometers, and a communications device; and
an application executable on a mobile device adapted to communicate with one or more of the plurality of wearable bands and to determine an activity of a wearer of the plurality of wearable bands based on information transmitted by the wearable bands,
wherein the application executable on the mobile device is operative to determine that the user has efficiently completed a task, and
wherein the application executable on the mobile device includes an authentication module and a workflow program, wherein the authentication module is operative to aggregate information transmitted by the wearable bands and provide authenticated activity information to the workflow program, and wherein the workflow program is operative to pay an employee wearing the bands based on the authenticated activity information.

17. The system of claim 16 wherein the application executable on the mobile device is operative to determine that the user is engaging in strenuous activity.

18. The system of claim 16 wherein the application executable on the mobile device is operative to determine that the user has achieved physical exhaustion.

* * * * *